(12) United States Patent
Numasawa et al.

(10) Patent No.: US 10,757,309 B2
(45) Date of Patent: Aug. 25, 2020

(54) ENDOSCOPE IMAGING MODULE WITH SIGNAL CABLE AND FLEXIBLE LINEAR STRUCTURE

(71) Applicant: FUJIKURA LTD., Tokyo (JP)

(72) Inventors: Yoshinobu Numasawa, Sakura (JP); Kenichi Ishibashi, Sakura (JP); Shingo Ishii, Tokyo (JP); Daisuke Murakami, Sakura (JP); Takeshi Ishizuka, Sakura (JP); Hideaki Usuda, Tokyo (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/116,655

(22) Filed: Aug. 29, 2018

(65) Prior Publication Data

US 2019/0068859 A1 Feb. 28, 2019

(30) Foreign Application Priority Data

Aug. 31, 2017 (JP) .................................. 2017-167984

(51) Int. Cl.
*H04N 5/225* (2006.01)
*A61B 1/05* (2006.01)
(Continued)

(52) U.S. Cl.
CPC ......... *H04N 5/2257* (2013.01); *A61B 1/0008* (2013.01); *A61B 1/00018* (2013.01);
(Continued)

(58) Field of Classification Search
CPC ...................................................... A61B 1/07
See application file for complete search history.

(56) References Cited

U.S. PATENT DOCUMENTS 4,646,721 A 3/1987 Arakawa
6,567,115 B1 * 5/2003 Miyashita .............. A61B 1/051
348/76
(Continued)

FOREIGN PATENT DOCUMENTS

FR 2737650 A1 2/1997
FR 2761561 A1 10/1998
(Continued)

OTHER PUBLICATIONS

Partial European Search Report issued in corresponding European Patent Application No. 18191358.3 dated Jan. 15, 2019 (13 pages).

*Primary Examiner* — Gary C Vieaux
(74) *Attorney, Agent, or Firm* — Osha Liang LLP

(57) ABSTRACT

An imaging module includes: an image-sensing device; a first substrate; a signal cable; a second substrate; and a flexible linear structure. Each of the first substrate and the second substrate includes a wiring and a cable terminal electrically connected to the signal cable on only one surface of the substrate. Each of the wiring of the first substrate and the wiring of the second substrate is electrically connected to the signal line via the cable terminal. The flexible linear structure extends in a direction along the signal cable from a front-end portion of the flexible linear structure supported by a structure-front-end support including the first substrate, and the flexible linear structure is disposed on a side of the signal cable where the first substrate and the second substrate are disposed.

8 Claims, 8 Drawing Sheets

(51) Int. Cl.
  *H01L 27/146* (2006.01)
  *A61B 1/07* (2006.01)
  *A61B 1/005* (2006.01)
  *A61B 1/00* (2006.01)
  *F21V 8/00* (2006.01)

(52) U.S. Cl.
  CPC ........ *A61B 1/0058* (2013.01); *A61B 1/00114* (2013.01); *A61B 1/00124* (2013.01); *A61B 1/00126* (2013.01); *A61B 1/051* (2013.01); *A61B 1/07* (2013.01); *H01L 27/14636* (2013.01); *H04N 5/2252* (2013.01); *H04N 5/2253* (2013.01); *H04N 5/2254* (2013.01); *H04N 5/2256* (2013.01); *A61B 1/00117* (2013.01); *G02B 6/005* (2013.01); *G02B 6/0008* (2013.01); *H04N 2005/2255* (2013.01)

(56) References Cited

U.S. PATENT DOCUMENTS

| | | | |
|---|---|---|---|
| 6,635,865 B1 * | 10/2003 | Soltyk | H04N 1/02805 |
| | | | 250/208.1 |
| 6,945,929 B2 * | 9/2005 | Ando | A61B 1/00114 |
| | | | 348/45 |
| 8,189,062 B2 * | 5/2012 | Irion | H04N 5/2251 |
| | | | 348/222.1 |
| 2006/0025651 A1 * | 2/2006 | Adler | A61B 1/00114 |
| | | | 600/110 |
| 2008/0214892 A1 | 9/2008 | Irion et al. | |
| 2010/0033559 A1 | 2/2010 | Yasunaga | |
| 2011/0034769 A1 * | 2/2011 | Adair | H04N 5/3765 |
| | | | 600/110 |
| 2011/0249106 A1 * | 10/2011 | Makino | H04N 5/2254 |
| | | | 348/76 |
| 2014/0009593 A1 * | 1/2014 | Segi | A61B 1/04 |
| | | | 348/76 |
| 2015/0378144 A1 * | 12/2015 | Handte | H04N 5/2251 |
| | | | 250/208.1 |
| 2016/0028926 A1 | 1/2016 | Ichimura et al. | |
| 2017/0035279 A1 * | 2/2017 | Fujii | A61B 1/00018 |
| 2017/0269348 A1 * | 9/2017 | Shinji | G02B 23/26 |
| 2018/0325360 A1 * | 11/2018 | Sekido | G02B 23/24 |

FOREIGN PATENT DOCUMENTS

| | | | | |
|---|---|---|---|---|
| JP | S62-098318 A | | 5/1987 | |
| JP | H10-099267 A | | 4/1998 | |
| JP | 11267095 A | * | 10/1999 | |
| JP | H11-267095 A | | 10/1999 | |
| JP | 2000199863 A | * | 7/2000 | ............ A61B 1/051 |
| JP | 3181503 B2 | | 7/2001 | |
| JP | 2006-109097 A | | 4/2006 | |
| JP | 2010-258582 A | | 11/2010 | |
| JP | 2015-173736 A | | 10/2015 | |
| WO | 2016-088267 A1 | | 6/2016 | |

* cited by examiner

ENDOSCOPE IMAGING MODULE WITH SIGNAL CABLE AND FLEXIBLE LINEAR STRUCTURE

CROSS REFERENCE TO RELATED APPLICATIONS

This application claims priority from Japanese Patent Application No. 2017-167984 filed on Aug. 31, 2017, the contents of which are incorporated herein by reference in their entirety.

BACKGROUND

Field of the Invention

The present invention relates to an imaging module that is available to an endoscope or the like and has a configuration in which a solid-state image sensing device is electrically connected to an electrical cable with a wiring substrate interposed therebetween.

Description of the Related Art

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2006-109097).

In this kind of imaging module, a plurality of ends of the electrical cable are electrically connected to wiring of the wiring substrate, and each electrical cable is electrically connected to the image-sensing device via the wiring of the wiring substrate.

In an imaging device such as an endoscope using the aforementioned imaging module, a configuration is often employed in which a plurality of electrical cables connected to an imaging module and a wiring substrate of the imaging module are accommodated in a tube. Furthermore, an back-end portion that is opposite to the imaging module side of the electrical cable of this imaging device is drawn from the tube and is electrically connected to an image information processing device that receives imaging signals from the electrical cable and displays an image on a display device such as a monitor.

However, there is a demand for multifunctional imaging devices. However, it was not easy to add, to such imaging device, a configuration having the function other than transmission of an imaging signal (transmission of an imaging signal to an image information processing device through an electrical cable), while avoiding an increase in diameter of a tube that accommodates the imaging module and the electrical cable therein.

SUMMARY

One or more embodiments of the invention provide an imaging module that can add a function other than transmission of an imaging signal thereto while preventing an increase in a diameter of a tube.

An imaging module according to one or more embodiments of the invention includes: an image-sensing device; a first substrate provided on a back surface side that is opposite to an imaging surface of the image-sensing device so as to extend from the image-sensing device to the opposite side of the imaging surface; a signal cable including: a signal line electrically connected to the image-sensing device via a wiring of the first substrate; and an outer coating accommodating the signal line; a second substrate having a wiring that is electrically connected to a rear end opposite to a front end of the signal line connected to the wiring of the first substrate; and a flexible linear structure provided along the signal cable. Each of the first substrate and the second substrate has a cable terminal electrically connected to the signal line of the signal cable only on one surface of each of the first substrate and the second substrate. Each of the wirings of the first substrate and the second substrate is electrically connected to the signal line via the cable terminal. In a state where the signal cable extends straight without torsional deformation, where a surface of the first substrate on which the cable terminal is located is defined as an upper face, and a surface opposite to the upper face of the first substrate is defined as a lower face, the imaging module is configured so that a surface of the second substrate on which the cable terminal is located is an upper face and so that a surface opposite to the upper face of the second substrate is a lower face. The linear structure extends in a direction along the signal cable from a front-end portion supported by a structure-front-end support including the first substrate, and the linear structure is disposed on the side of the signal cable at which the first substrate and the second substrate are provided.

In the imaging module according to one or more embodiments of the invention, the structure-front-end support may include: the first substrate; and a light guide made of a transparent resin into which the first substrate is implanted, wherein the linear structure may be an optical fiber, and a front-end portion of the optical fiber may be fixed to the light guide in a state of being inserted thereinto.

In the imaging module according to one or more embodiments of the invention, the light guide may include an optical path changer that reflects, refracts, or scatters emitted light emitted from a front end of the optical fiber, and thereby outputs the light from the light guide to the outside thereof.

In the imaging module according to one or more embodiments of the invention, a part or an entirety of the linear structure may be formed of a current-passage-heating shape-memory alloy.

In the imaging module according to one or more embodiments of the invention, a part or an entirety of the linear structure may be formed of a current-passage-heating shape-memory alloy, and a back-end portion of the linear structure may be attached to the second substrate.

In the imaging module according to one or more embodiments of the invention, a front-end portion of the linear structure may be formed on a second surface side opposite to a first surface of a first substrate main body on which the cable terminal of the first substrate is formed.

In the imaging module according to one or more embodiments of the invention, the first substrate, a front-end portion of the linear structure, and the structure-front-end support may be located within a projected area of the image-sensing device which is projected toward the back surface side.

In the imaging module according to one or more embodiments of the invention, a wiring of the first substrate may include: a first substrate upper face wiring that is formed on a first surface of a first substrate main body on which the cable terminal of the first substrate is provided; a first substrate lower face wiring that is formed on a second surface opposite to the first surface; and a through-hole interconnection that penetrates through the first surface and the second surface and electrically connects the first substrate upper face wiring to the first substrate lower face wiring. The image-sensing device may include a plurality of image-sensing device electrodes provided on the back surface, and each image-sensing device electrode may be arranged on both sides of the first substrate in a thickness direction, and each of the first substrate upper face wiring and the first substrate lower face wiring of the first substrate may be electrically connected to the image-sensing device electrode.

In the imaging module according to one or more embodiments of the invention, the signal cable may include a plurality of signal lines that are laterally disposed inside the outer coating, and the first substrate and the second substrate may be attached to the signal cable on the same side with respect to an array plane of the plurality of the signal lines of the signal cable and are directed along the array plane.

As described above, according to one or more embodiments of the invention, in the case of accommodating the imaging module in a tube, it is only necessary to use a tube in which a cross sectional size required for accommodating the image-sensing device is ensured, and it is possible to add a function other than transmission of an imaging signal to the imaging module while preventing an increase in a diameter of the tube used for accommodating the linear structure.

DETAILED DESCRIPTION

Figure 1:
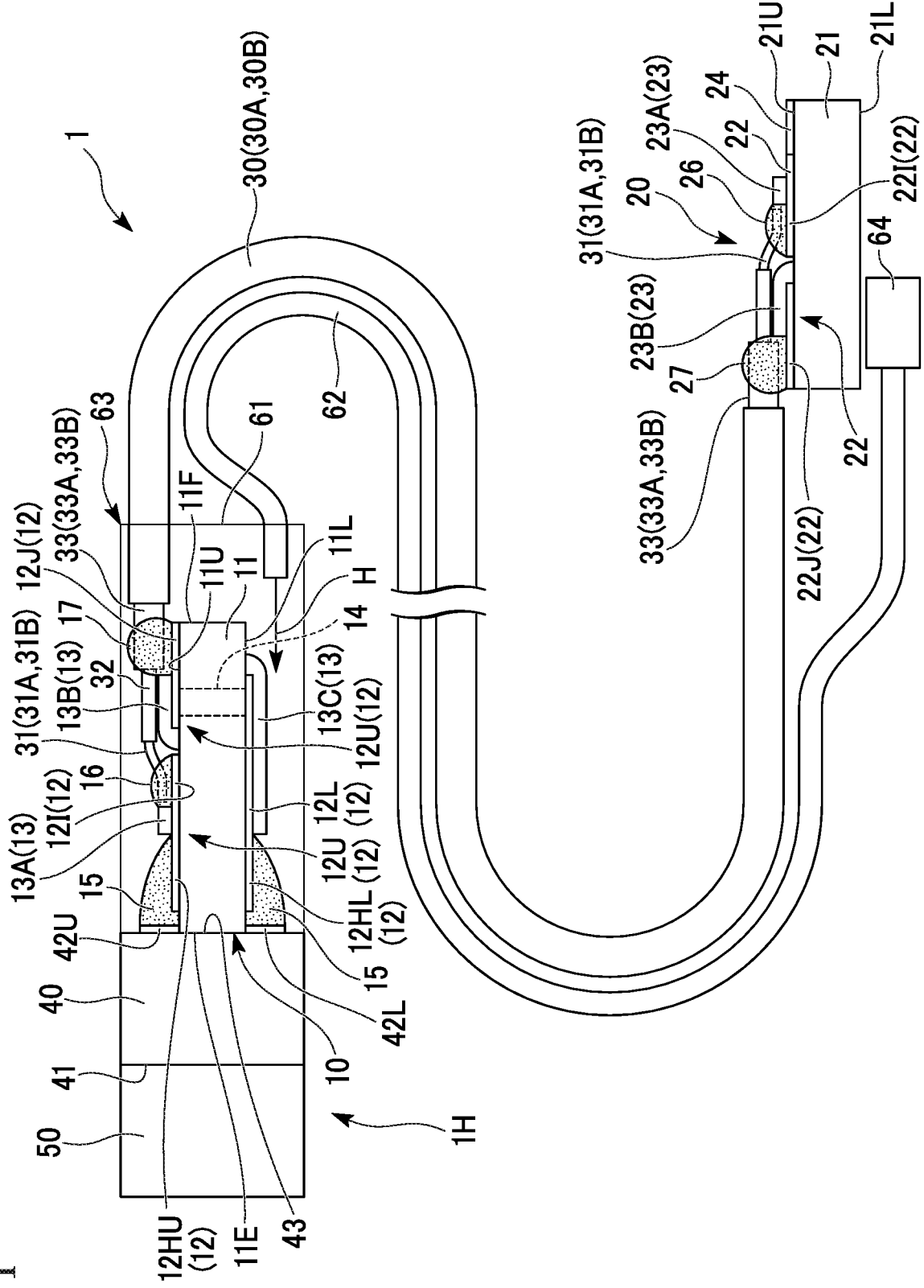
FIG. 1 is a view showing a schematic configuration of an imaging module according to one or more embodiments of the invention.

Hereinafter, embodiments of the invention will be described with reference to drawings.

In the drawings showing embodiments of the invention, in order for the respective components to be of understandable size in the drawings, the dimensions and the proportions of the components are modified as needed compared with the real components.

FIG. 1 is a view showing a schematic configuration of the imaging module 1 according to one or more embodiments of the invention.

The imaging module 1 includes a first substrate 10, a second substrate 20, a signal cable 30, a solid-state image sensing device 40 (image-sensing device), a lens housing 50, a light guide 61, and an optical fiber 62 (linear structure). (First Substrate 10)

The first substrate 10 includes a first substrate main body 11 serving as an insulating member and a first wiring 12 (upper face wiring 12U, lower face wiring 12L, and through-hole interconnection 14) formed on the first substrate main body 11. The first substrate main body 11 has an upper face 11U (first surface) and a lower face 11L (second surface) opposite to the upper face 11U. The upper face wiring 12U is formed on the upper face 11U. The lower face wiring 12L is formed on the lower face 11L. The upper face wiring 12U and the lower face wiring 12L include a conductive wiring pattern.

The first substrate 10 is disposed on an electrode surface 43 (back surface) of the solid-state image sensing device 40 which is opposite to an imaging surface 41 thereof and extends in a direction substantially orthogonal to the electrode surface 43 (a direction opposite to the imaging surface 41).

The first substrate main body 11 (first substrate 10) has a front-edge face 11E (end face) provided near the solid-state image sensing device 40 and a rear-edge face 11F opposite to the front-edge face 11E. The front-edge face 11E of the first substrate 10 is disposed so as to be in contact with the electrode surface 43 of the solid-state image sensing device 40 or close to the electrode surface via a slight space. The rear-edge face 11F is exposed to a space adjacent to the signal cable 30.

The first substrate 10 includes a through-hole interconnection 14 that penetrates through the first substrate main body 11 between the upper face 11U and the lower face 11L. The through-hole interconnection 14 electrically connects the upper face wiring 12U to the lower face wiring 12L.

An electrode terminal 12HU that is electrically connected to the upper face wiring 12U is formed on the upper face 11U. An electrode terminal 12HL that is electrically connected to the lower face wiring 12L is formed on the lower face 11L. That is, electrode terminals are formed on both the upper face 11U and the lower face 11L. The electrode terminal 12HU is electrically connected via solder 15 to an image-sensing device electrode 42U (42) of the solid-state image sensing device 40 which will be described later. The electrode terminal 12HL is electrically connected to an image-sensing device electrode 42L (42) of the solid-state image sensing device 40 via the solder 15.

A center conductor terminal 12I (first cable terminal) and an external conductor terminal 12J (first cable terminal) are formed only on one surface of the first substrate main body 11, that is, only on the upper face 11U. The center conductor terminal 12I and the external conductor terminal 12 are electrically connected to the upper face wiring 12U. However, the upper face wiring 12U has not only a wiring pattern that electrically connects the center conductor terminal 12I to the electrode terminal 12HL but also a wiring pattern that electrically connects the external conductor terminal 12J and the electrode terminal 12HL. The electrode terminal 12HL to which the center conductor terminal 12I is electrically connected via the wiring pattern is different from the electrode terminal 12HL to which the external conductor terminal 12J is electrically connected.

The center conductor terminal 12I is electrically connected via solder 16 to a center conductor 31 of the signal cable 30 which will be described later. The external conductor terminal 12J is electrically connected via solder 17 to an external conductor 33 of the signal cable 30.

Upper face resists 13A and 13B (13) are formed on the upper face 11U of the first substrate main body 11 so as to coat a surface of the upper face wiring 12U. The upper face resist 13A is formed between the solder 15 and the solder 16.

The upper face resist 13B is formed between the solder 16 and the solder 17. A lower face resist 13C (13) is formed on the lower face 11L of the first substrate main body 11 so as to coat a surface of the lower face wiring 12L.

In FIG. 1, as seen in the direction from the solid-state image sensing device 40 toward the rear-edge face 11F, the signal cable 30 is disposed within an outline of the solid-state image sensing device 40 on a plane of projection, and the signal cable 30 does not partially protrude from the outline of the solid-state image sensing device 40 shown in the plane of projection of the solid-state image sensing device 40.

(Second Substrate 20)

The second substrate 20 includes a second substrate main body 21 serving as an insulating member and a second wiring 22 formed on the second substrate main body 21. The second substrate main body 21 has an upper face 21U (one of the surfaces). A center conductor terminal 22I (second cable terminal) and an external conductor terminal 22J (second cable terminal) are formed on the upper face 21U. The center conductor terminal 22I and the external conductor terminal 22J are electrically connected to the inter-terminal wirings that are provided so as to correspond to each of the center conductor terminal 22I and the external conductor terminal 22J of the second wiring 22.

The center conductor terminal 22I is electrically connected via solder 26 to the center conductor 31 of the signal cable 30. The external conductor terminal 22J is electrically connected via solder 27 to the external conductor 33 of the signal cable 30.

Resists 23A and 23B (23) are formed on the upper face 21U of the second substrate main body 21 so as to coat a surface of the second wiring 22. The resist 23B is formed between the solder 26 and the solder 27. The resist 23A is formed close to the solder 26 on the center conductor terminal 22I.

The second substrate 20 includes an external connection terminal 24 formed on the second substrate main body 21. The second substrate 20 has the external connection terminals 24 having the same number as the total number of the center conductor terminal 22I and the external conductor terminal 22J which are provided on the second substrate 20. The center conductor terminal 22I and the external conductor terminal 22J are electrically connected via the inter-terminal wirings of the second wiring 22 to the external connection terminals 24 which correspond to the center conductor terminal and the external conductor terminal.

An external device (not shown in the figure) is electrically connected to the external connection terminal 24. The external device that is electrically connected to the external connection terminal 24 is electrically connected to the center conductor 31 or the external conductor 33 of a coaxial cable of the signal cable 30 via the inter-terminal wiring of the second wiring 22. Moreover, the external device is also electrically connected to the solid-state image sensing device 40 via the center conductor 31 or the external conductor 33 and via the first wiring 12 of the first substrate 10.

Note that, the external connection terminal 24 and the second wiring 22 are simultaneously formed on the second substrate main body 21.

(Solid-State Image Sensing Device 40 and Lens Housing 50)

The solid-state image sensing device 40 includes the imaging surface 41, the electrode surface 43, and the image-sensing device electrodes 42U and 42L that are provided on the electrode surface 43. The image-sensing device electrodes 42U and 42L are each formed in a pad shape that extends along the electrode surface 43 of the solid-state image sensing device 40. The front-end portion of the first substrate 10 (portion at which the front-edge face 11E is located) is attached to the solid-state image sensing device 40 via the solder 15 so as to be located between the image-sensing device electrodes 42U and 42L in a surface direction of the electrode surface 43 (directions parallel to the electrode surface).

The solder 15 connects the image-sensing device electrode 42U and the electrode terminal 12HU which are substantially orthogonal to each other, and connects the image-sensing device electrode 42L and the electrode terminal 12HL which are substantially orthogonal to each other.

FIG. 1 shows the image-sensing device electrodes 42U and 42L which are arranged at the upper position and the lower position, respectively; however, when seen in a plan view of the electrode surface 43 (in a plan view showing the electrode surface 43 when viewed in a vertical direction) four image-sensing device electrodes 42 are arranged on the electrode surface 43. That is, two image-sensing device electrodes 42U and two image-sensing device electrodes 42L are formed on the electrode surface 43.

Note that, the number of each of the image-sensing device electrodes 42U and 42L which are provided on both sides in the thickness direction of the first substrate 10 is not limited and may be appropriately selected.

The lens housing 50 is connected to the imaging surface 41, and a lens unit such as an object lens is mounted on the lens housing 50. As the solid-state image sensing device 40, for example, a CMOS (complementary metal oxide semiconductor) may be used.

(Signal Cable 30)

Figure 2:
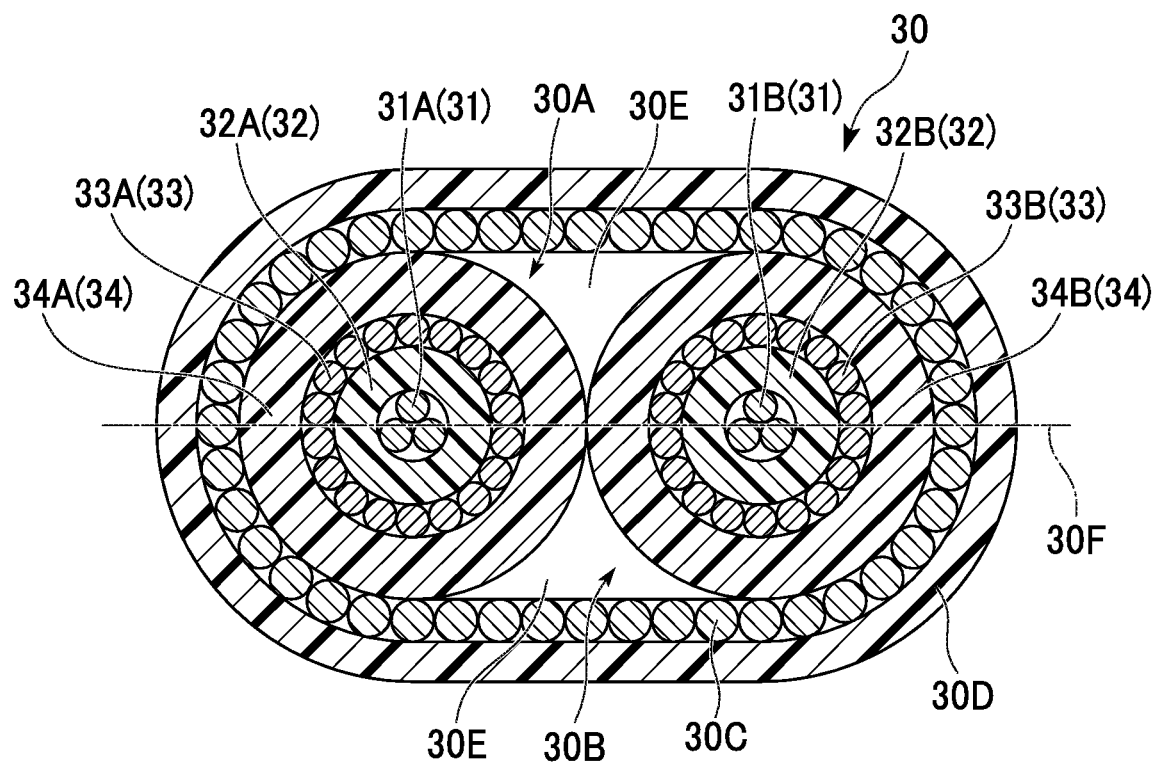
FIG. 2 is a cross-sectional view showing a signal cable of the imaging module shown in FIG. 1.

FIG. 2 is a cross-sectional view showing the signal cable 30 of the imaging module according to one or more embodiments of the invention.

The signal cable 30 is provided between the first substrate 10 and the second substrate 20 and includes two coaxial cables (signal line, a first coaxial cable 30A, a second coaxial cable 30B), a shield conductor 30C that surrounds the first coaxial cable 30A and the second coaxial cable 30B, and an outer coating 30D that surrounds the shield conductor 30C. The shield conductor 30C is provided on the entire inner peripheral surface of the outer coating 30D and is formed in a layer shape.

In FIG. 2, for example, the structure is shown in which the shield conductor 30C is disposed separately from a cable contact portion at which the side portions of the first coaxial cable 30A and the second coaxial cable 30B are in contact with each other, and a space 30E is present between the cable contact portion and the shield conductor 30C located at both sides of the cable contact portion. However, as a cross-sectional structure of the signal cable 30, a cross-sectional structure is applicable, in which the shield conductor 30C enters a region of the space 30E shown in FIG. 2 and a space is substantially absent among the first coaxial cable 30A, the second coaxial cable 30B, and the layer-shaped shield conductor 30C.

Each of the coaxial cables 30A and 30B includes a center conductor 31 (31A, 31B), an internal insulator 32 (32A, 32B), an external conductor 33 (33A, 33B), and an external insulator 34 (34A, 34B). For example, the center conductor 31 is used as a signal line that supplies a signal to the solid-state image sensing device 40, and the external conductor 33 is used as a power supply line that supplies electric power to the solid-state image sensing device 40.

The center conductor 31 (31A, 31B) electrically connects the center conductor terminal 12I of the first substrate 10 to the center conductor terminal 22I of the second substrate 20.

The external conductor 33 (33A, 33B) electrically connects the external conductor terminal 12J of the first substrate 10 to the external conductor terminal 22J of the second substrate 20.

The shield conductor 30C and the outer coating 30D surrounds the first coaxial cable 30A and the second coaxial cable 30B over the entire signal cable 30. However, the outer coating 30D is removed at the position close to the first substrate 10 and the second substrate 20, and the first coaxial cable 30A and the second coaxial cable 30B are exposed.

Furthermore, as shown in FIG. 1, the external conductor 33 and the center conductor 31 which constitute each of the first coaxial cable 30A and the second coaxial cable 30B are exposed so as to correspond to wiring patterns of the first substrate 10 and the second substrate 20.

Furthermore, the shield conductor 30C of the signal cable 30 extends from an end of the outer coating 30D at an end portion (back-end portion) of the signal cable 30 which is close to the second substrate 20 and is electrically connected to a shield terminal (not shown in the figure) formed on the upper surface side of the second substrate 20 (the upper face 21U of the second substrate main body 21). A grounding terminal electrically connected to a grounding external circuit located outside the imaging module and an inter-terminal wiring that electrically connects the shield terminal and the grounding terminal are also formed on the second substrate 20. Consequently, in the case where the grounding external circuit is electrically connected to the grounding terminal of the second substrate 20, the shield conductor 30C of the signal cable 30 is electrically connected to the grounding external circuit via the shield terminal of the second substrate 20, the inter-terminal wiring, and the grounding terminal. The imaging module can be used in a state where the shield conductor 30C of the signal cable 30 is electrically connected to the grounding external circuit connected to the grounding terminal of the second substrate 20.

Note that, in the imaging module, it is not essential that the shield conductor 30C of the signal cable 30 is electrically connected to the grounding external circuit, and it can be omitted. In the case where the shield conductor 30C of the signal cable 30 is not electrically connected to the grounding external circuit, the second substrate 20 on which the shield terminal, the grounding terminal, and the inter-terminal wiring that electrically connects the shield terminal and the grounding terminal are not formed can be used.

(Wiring Pattern on First Substrate 10)

FIGS. 4A and 4B are views each showing a wiring pattern formed on the first substrate of the imaging module according to one or more embodiments of the invention. FIG. 4A shows a wiring pattern of the upper face wiring 12U (first substrate upper face wiring) formed on the upper face 11U of the first substrate main body 11. FIG. 4B shows a wiring pattern of the lower face wiring 12L formed on the lower face 11L of the first substrate main body 11. FIG. 4B is not a bottom view showing the lower face 11L but is a projection view as seen from the upper face 11U shown in FIG. 4A. Consequently, the broken line part shown in FIG. 4A corresponds to the solid line part shown in FIG. 4B.

Figure 4:
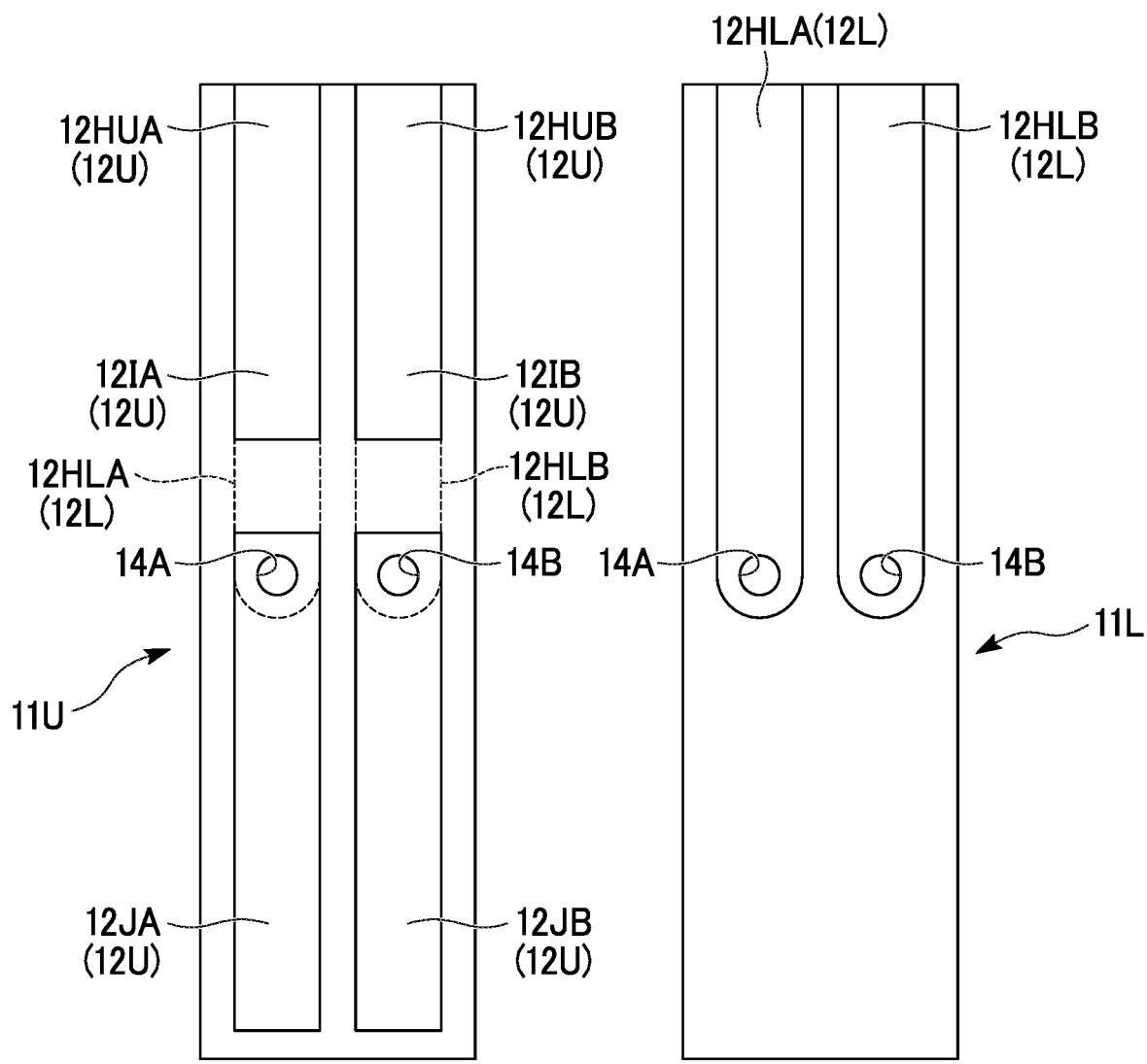
FIG. 4A is a view showing a wiring pattern formed on the first substrate of the imaging module shown in FIG. 1 and is an explanatory view showing a connection structure between an image-sensing device and the signal cable.
FIG. 4B is a view showing a wiring pattern formed on the first substrate of the imaging module shown in FIG. 1 and is an explanatory view showing a connection structure between an image-sensing device and the signal cable.

Note that, as shown in FIG. 1, the upper face resists 13A and 13B and the lower face resist 13C are formed on the upper face 11U and the lower face 11L of the first substrate main body 11; however, in FIG. 4, the resists 13A, 13B, and 13C are omitted.

Reference numeral 12JA corresponds to the external conductor terminal 12J and is a terminal connected to the external conductor 33A of the first coaxial cable 30A via the solder 17. Hereinbelow, it will be referred to as an external conductor terminal 12JA. Reference numeral 12JB corresponds to the external conductor terminal 12J, and is a terminal connected to the external conductor 33B of the second coaxial cable 30B via the solder 17. Hereinbelow, it will be referred to as an external conductor terminal 12JB.

Reference numeral 121A corresponds to the center conductor terminal 12I and is a terminal connected to the center conductor 31A of the first coaxial cable 30A via the solder 16. Hereinbelow, it will be referred to as a center conductor terminal 121A. Reference numeral 121B corresponds to the center conductor terminal 12I and is a terminal connected to the center conductor 31B of the second coaxial cable 30B via the solder 16. Hereinbelow, it will be referred to as a center conductor terminal 12IB.

Reference numeral 12HUA is a terminal corresponding to the electrode terminal 12HU and hereinbelow will be referred to as an electrode terminal 12HUA. Reference numeral 12HUB is a terminal corresponding to the electrode terminal 12HU and hereinbelow will be referred to as an electrode terminal 12HUB.

Reference numeral 12HLA is a terminal corresponding to the electrode terminal 12HL and hereinbelow will be referred to as an electrode terminal 12HLA. Reference numeral 12HLB is a terminal corresponding to the electrode terminal 12HL and hereinbelow will be referred to as an electrode terminal 12HLB. Reference numerals 14A and 14B correspond to the through-hole interconnection 14 and hereinbelow will be referred to as through-hole interconnections 14A and 14B.

As shown in FIG. 4A, the external conductor terminal 12JA is electrically connected to the through-hole interconnection 14A. Similarly, the external conductor terminal 12JB is electrically connected to the through-hole interconnection 14B. Furthermore, the center conductor terminal 12IA is electrically connected to the electrode terminal 12HUA. Similarly, the center conductor terminal 121B is electrically connected to the electrode terminal 12HUB.

The external conductor terminals 12JA and 12JB, the center conductor terminals 121A and 121B, and the electrode terminals 12HUA and 12HUB can be collectively formed by patterning using a known photolithographic technique or the like.

As shown in FIG. 4B, the through-hole interconnection 14A is electrically connected to the electrode terminal 12HLA. Similarly, the through-hole interconnection 14B is electrically connected to the electrode terminal 12HLB. That is, the external conductor terminal 12JA formed on the upper face 11U is electrically connected to the electrode terminal 12HLA formed on the lower face 11L with the through electrode 14A interposed therebetween. Moreover, the external conductor terminal 12JB formed on the upper face 11U is electrically connected to the electrode terminal 12HLB formed on the lower face 11L with the through-hole interconnection 14B interposed therebetween.

The electrode terminals 12HLA and 12HLB can be collectively formed by patterning using a known photolithographic technique or the like.

Also, the through-hole interconnections 14A and 14B can also be formed by a known method.

Next, an electrical connection structure of the first coaxial cable 30A and the second coaxial cable 30B with respect to the image-sensing device electrode 42 will be described.

As shown in FIGS. 1 and 4A, the center conductor 31A of the first coaxial cable 30A is electrically connected to the center conductor terminal 121A via the solder 16. In addition, the center conductor 31B of the second coaxial cable 30B is electrically connected to the center conductor terminal 121B via the solder 16.

Consequently, the center conductor 31A is connected to the image-sensing device electrode 42U (42UA) via the center conductor terminal 121A and the electrode terminal 12HUA, and the center conductor 31B is connected to the image-sensing device electrode 42U (42UB) via the center conductor terminal 121B and the electrode terminal 12HUB.

Here, the image-sensing device electrode 42UA is one electrode of two image-sensing device electrodes 42U, that is, an electrode connected to the center conductor 31A of the first coaxial cable 30A. The image-sensing device electrode 42UB is the other electrode of the two image-sensing device electrodes 42U, that is, an electrode connected to the center conductor 31B of the second coaxial cable 30B.

As shown in FIGS. 1, 4A, and 4B, the external conductor 33A of the first coaxial cable 30A is electrically connected to the external conductor terminal 12JA via the solder 17. Furthermore, the external conductor 33B of the second coaxial cable 30B is electrically connected to the external conductor terminal 12JB via the solder 17. The external conductor terminal 12JA is electrically connected to the electrode terminal 12HLA via the through-hole interconnection 14A. The external conductor terminal 12JB is electrically connected to the electrode terminal 12HLB via the through-hole interconnection 14B.

Therefore, the external conductor 33A is connected to the image-sensing device electrode 42L (42LA) via the external conductor terminal 12JA and the electrode terminal 12HLA, and the external conductor 33B is connected to the image-sensing device electrode 42L (42LB) via the external conductor terminal 12JB and the electrode terminal 12HLB. Here, the image-sensing device electrode 42LA is one electrode of two image-sensing device electrodes 42L, that is, an electrode connected to the external conductor 33A of the first coaxial cable 30A. The image-sensing device electrode 42LB is the other electrode of the two image-sensing device electrodes 42L, that is, an electrode connected to the external conductor 33B of the second coaxial cable 30B.

Note that, the first wiring 12 which is shown in FIGS. 4A and 4B as an example (the upper face wiring 12U, the lower face wiring 12L, the through-hole interconnection 14) has the configuration in which a wiring pattern having two lines that linearly extend straight in the extending direction of the first substrate main body 11 is formed on each of the upper face 11U and the lower face 11L of the first substrate main body 11; however, the invention is not limited to the above-described linear wiring pattern. The first wiring 12 may has a cross pattern such that the first line of the wiring provided on the upper face 11U is connected to the second line of the wiring provided on the lower face 11L and the second line of the wiring provided on the upper face 11U is connected to the first line of the wiring provided on the lower face 11L.

(Light Guide 61, Optical Fiber 62, Structure-Front-End Support 63)

The imaging module 1 shown in FIG. 1 also includes the optical fiber 62 (linear structure) that extends along the signal cable 30 and a structure-front-end support 63 having a structure in which the entire first substrate 10 is implanted into the light guide 61 made of a transparent resin.

The light guide 61 shown in FIG. 1 is formed so that the outer coating 30D located at the front-end portion of the signal cable 30, the center conductor 31 protruding from the end of the outer coating 30D, and the entire protruding portion such as the external conductor 33 are implanted into the resin forming the light guide 61.

The optical fiber 62 is a linear structure provided along the signal cable 30. The end (front-end portion) located near the solid-state image sensing device 40 of the optical fiber 62 is implanted and fixed in a transparent resin that forms the light guide 61. The front-end portion of the optical fiber 62 is fixed in a state of being inserted to the light guide 61 from the back side thereof (the opposite side of the front side of the solid-state image sensing device 40) in a direction along the front-back direction of the first substrate 10 (a direction perpendicular to the electrode surface 43 of the solid-state image sensing device 40).

The optical fiber 62 extends so that the portion between the front-end portion thereof fixed to (supported by) the light guide 61 and the back side portion is located along the signal cable 30. The light guide 61 has a function as a support member (front-end support member for a linear structure) that fixes (supports) the front-end portion of the optical fiber 62 and is used to be attached to the first substrate 10.

Note that, not only the front-end portion of the optical fiber 62 is directly implanted into and fixed to a transparent resin that forms the light guide 61 but also a structure may be adopted in which, for example, the front-end portion of the optical fiber is inserted into a hole which is formed in the light guide 61 so as to extend from the back end to the front end and is fixed to the light guide 61 by adhesive.

In FIG. 1, in the vertical direction of the structure-front-end support 63 (in the vertical direction in FIG. 1, the upper side in FIG. 1 is the upper side in the vertical direction, and the lower side in FIG. 1 is the lower side in the vertical direction) which coincides with the thickness direction of the first substrate 10, the front-end portion of the optical fiber 62 is fixed to the light guide 61 at the side opposite to the signal cable 30 on the first substrate 10, that is, at the lower side of the first substrate 10. However, the position in the vertical direction of the structure-front-end support 63 with respect to the light guide 61 of the front-end portion of the optical fiber 62 may be other than the lower side of the first substrate 10.

The structure-front-end support 63 of the imaging module 1 shown in FIG. 1 is located within a projected area of the solid-state image sensing device 40 which is projected toward the back surface side.

Hereinbelow, regarding the solid-state image sensing device 40, the direction (vertical direction in FIG. 1) that coincides with the thickness of the first substrate 10 is referred to as a thickness direction. The thickness of the first substrate 10 is less than or equal to half of the length in the thickness direction of the solid-state image sensing device 40. The first substrate 10 is attached to the center of the electrode surface 43 of the solid-state image sensing device 40 in the vertical direction that coincides with the thickness direction of the solid-state image sensing device 40 so that the upper face 11U and the lower face 11L are perpendicular to the vertical direction of the electrode surface 43.

The entire of the first substrate 10 is located within a projected area of the solid-state image sensing device 40 which is projected toward the back surface side.

The portions of the signal cable 30 and the optical fiber 62 which are located in the light guide 61 are located within a projected area of the solid-state image sensing device 40 which is projected toward the back surface side.

The light guide 61 is formed so that the entire of the light guide 61 is located within a projected area of the solid-state image sensing device 40 which is projected toward the back surface side.

The imaging module 1 shown in FIG. 1 includes a front head 1H (front-end portion) that is constituted of the lens housing 50, the solid-state image sensing device 40, the structure-front-end support 63.

Figure 5:
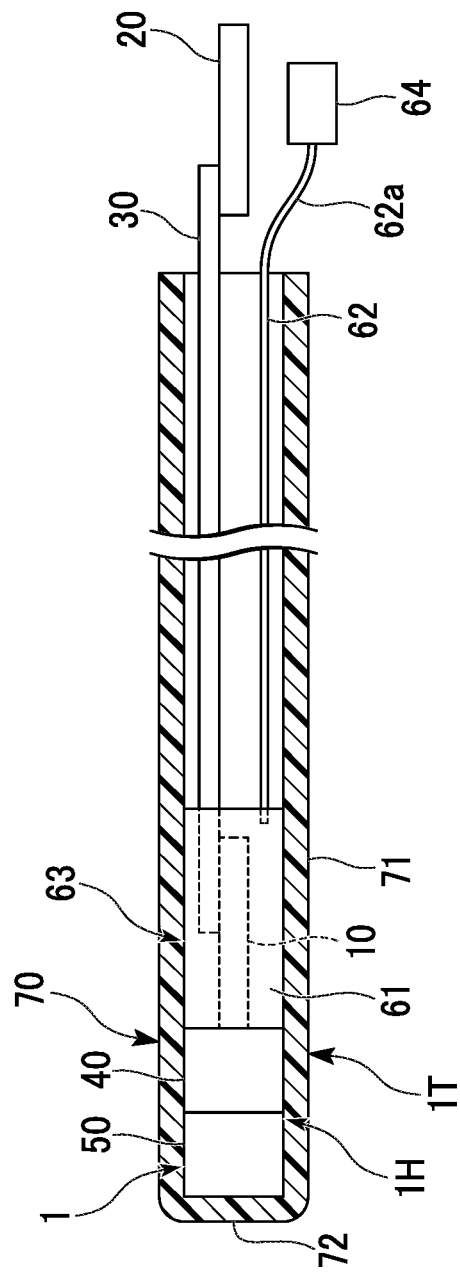
FIG. 5 is a cross-sectional view showing a schematic configuration of an example of a tube-attached imaging module having the imaging module shown in FIG. 1 accommodated in a tube.

As shown in FIG. 5, the imaging module 1 is used in a state of being accommodated in a protection tube 70 (tube) (tube-attached imaging module 1T).

As shown in FIG. 5, the protection tube 70 is a flexible tube made of, for example, a synthetic resin material such as silicone resin.

As a material used to form the protection tube 70, not only silicone resin but also polyurethane, polyethylene, polytetrafluoroethylene (PTFE), or the like may be adopted.

The protection tube 70 includes a tubular part 71 and a front end wall 72 that seals one end (front-end portion) of the tubular part 71 in the axis direction. The rear end of the protection tube 70 which is opposite to the front end wall 72 (the other end in the axis direction of the tubular part 71) is opened.

Note that, in the description, in the following explanation regarding the protection tube 70 and the tubular part 71, the portion close to the front end wall 72 is referred to as a front side, and the portion opposite thereto is referred to as a back side.

The tubular part 71 of the protection tube 70 shown in FIG. 5 extends and has a fixed size in cross section in the overall length. However, the structure of the tubular part 71 may be adopted in which, for example, the portion other than the back-end portion of the tubular part 71 (tubular main section) is formed so as to extend so as to have a fixed size in cross section and the back-end portion is formed so as to have a size in cross section which is larger than that of the tubular main section.

As shown in FIG. 5, the back-end portion (end portion close to the second substrate 20) of the signal cable 30 and the back-end portion of the optical fiber 62 extend from the rear end of the protection tube 70. The second substrate 20 is not accommodated in the protection tube 70.

The protection tube 70 of the tube-attached imaging module 1T shown in FIG. 5 accommodates the entire imaging module 1 therein with the exception of: the portions of the signal cable 30 and the optical fiber 62 which form the imaging module 1 and are extended from the rear end of the protection tube 70; and the second substrate 20.

In FIG. 5, the front end wall 72 of the protection tube 70 is disposed so as to come into contact with the front-edge face of the lens housing 50 of the imaging module 1 (end face opposite to the solid-state image sensing device 40). However, the front end wall 72 of the protection tube 70 may be disposed so that a slight space is provided in front of the lens housing 50 of the imaging module 1 (which is provided opposite to the solid-state image sensing device 40). The front end wall 72 of the protection tube 70 functions as a cover wall that covers the front side of the lens housing 50 of the imaging module 1.

Note that, the front-end portion of the protection tube 70 which accommodates the front head 1H of the imaging module 1 therein (including the front end wall 72) is transparent. The solid-state image sensing device 40 receives light that passes through the front-end portion of the protection tube 70 from the outside thereof via a lens unit provided inside the lens housing 50 and captures an image.

The front end (rear end of the optical fiber 62) of the back side extending portion 62a of the optical fiber 62 extended from the rear end of the protection tube 70 is connected to a light output device 64. The optical fiber 62 transmits the output light which is output from the light output device 64 and enters the end face of the optical fiber 62 and emits the light from the front-edge face (end face of front-end portion). The light H (emission light) emitted from the front-edge face of the optical fiber 62 is output from the light guide 61 to the outside thereof due to, for example, inclination of the front-end portion of the optical fiber 62 with respect to the first substrate 10, reflection, scattering, or the like, which occurs in the light guide 61. The light that is emitted from the front-edge face of the optical fiber 62 and is output from the light guide 61 to the outside passes through the front-end portion of the transparent protection tube 70 and is output from the front-end portion of the protection tube 70 to the outside thereof. The light that is output from the front-end portion of the protection tube 70 to the outside thereof can be utilized as illuminating light that illuminates the inside of a space such as a duct or a gap which is inserted into the front-end portion of the tube-attached imaging module 1T (the portion at which the front-end portion of the protection tube 70 is located). The optical fiber 62 is a linear structure having a function of illuminating, with light, the space into which the front-end portion of the tube-attached imaging module 1T is inserted.

(Positional Relationship Among First Substrate 10, Second Substrate 20, Signal Cable 30, and Optical Fiber 62)

Figure 3:
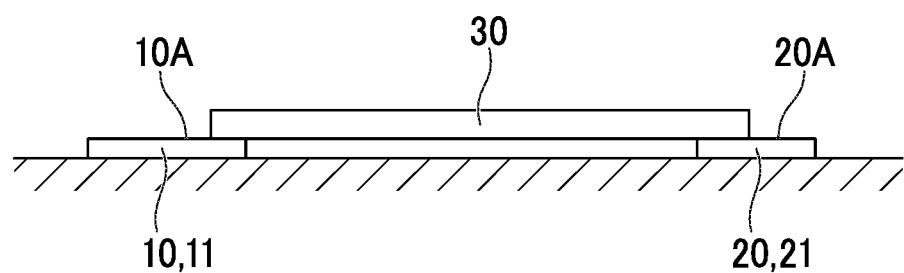
FIG. 3 is a view showing a schematic configuration of the imaging module shown in FIG. 1 and is an explanatory view showing a positional relationship among a first substrate, a second substrate, and the signal cable.

FIG. 3 is a view showing a schematic configuration of the imaging module according to one or more embodiments of the invention and is an explanatory view showing a positional relationship among the first substrate 10, the second substrate 20, and the signal cable 30.

As shown in FIG. 3, in a state where the signal cable 30 extends straight without torsional deformation, where a surface 10A of the first substrate 10 on which the first cable terminals 12I and 12J are provided is defined as an upper face, and a surface opposite to the upper face of the first substrate is defined as a lower face, the imaging module 1 is configured so that a surface 20A of the second substrate 20 on which the second cable terminals 22I and 22J are provided is defined as an upper face and so that a surface opposite to the upper face of the second substrate is defined as a lower face. Accordingly, as shown in FIG. 3, in a state where the lower face of each of the first substrate 10 and the second substrate 20 are in contact with the same horizontal plane, the first substrate 10 and the second substrate 20 can be mounted on the same horizontal plane. As shown in FIG. 3, when the lower faces of the first substrate 10 and the second substrate 20 are in contact with the same horizontal plane and are mounted on the same horizontal plane, the signal cable 30 is located at the upper side of the first substrate 10 and the second substrate 20.

As shown in FIG. 3, in a state where the first substrate main body 11 constituting the first substrate 10 and the second substrate main body 21 constituting the second substrate 20 are fixed on the same horizontal plane, the signal cable 30 can be connected to each the surfaces 10A and 20A, and it is possible to simplify a step of manufacturing the imaging module 1.

The first substrate 10 and the second substrate 20 are attached to the signal cable 30 on the same surface as each other on a surface on which the coaxial cables 30A and 30B (signal line) of the signal cable 30 are provided so that the directions thereof with respect to the signal cable 30 are substantially the same as each other.

As shown in FIG. 2, the signal cable 30 has a configuration in which a plurality of coaxial cables 30A and 30B (signal line) are laterally disposed inside the outer coating 30D. The first substrate 10 and the second substrate 20 are attached to the signal cable 30 on the same side with respect to an array plane 30F of the coaxial cables 30A and 30B of the signal cable 30 and are directed along the array plane 30F.

In the tube-attached imaging module 1T shown in FIG. 5, it is possible to ensure an empty space in the area inside the protection tube 70 at the side of the signal cable 30 on which the first substrate 10 and the second substrate 20 are provided.

As shown in FIGS. 1 and 5, the portion of the optical fiber 62 (linear structure) which is located inside the protection tube 70 extends in a direction toward the signal cable 30 from the front-end portion supported by the light guide 61 of the structure-front-end support 63 and is disposed on the side of the signal cable 30 at which the first substrate 10 and the second substrate 20 are provided.

As compared with the case where, for example, the optical fiber 62 is arranged in parallel to the signal cable on the opposite side of the signal cable 30 on which the first substrate 10 and the second substrate 20 are provided, or as compared with the case where the optical fiber 62 is provided in a spiral shape on the outer-periphery of the signal cable 30, the tube-attached imaging module 1T shown in FIG. 5 can reduce the cross sectional size (a size in cross section) and the diameter of the protection tube 70 (specifically, a cross sectional size of the tubular part 71).

According to the aforementioned embodiments of the invention, the empty space is utilized which can be ensured in the area inside the protection tube 70 at the side of the signal cable 30 on which the first substrate 10 and the second substrate 20 are provided, it is possible to provide the optical fiber 62 (linear structure) in the empty space. Consequently, as the protection tube 70, it is possible to use a tube in which a cross sectional size required for accommodating the solid-state image sensing device 40 is ensured, and it is not necessary to increase a diameter of the protection tube for accommodating the optical fiber 62 therein.

The imaging module 1 can accommodate the optical fiber 62 in the protection tube 70 without an increase in a diameter of the protection tube 70 and can allow the tube-attached imaging module 1T to have a function of illuminating, with light, a space into which the front-end portion thereof is inserted.

The entire light guide 61 of the structure-front-end support 63 which forms the imaging module 1 shown in FIG. 1 is made of only transparent resin. However, as the configuration of the light guide, a configuration may be adopted in which particles (light scattering particles) having a light scattering property such as metal particles are dispersed and mixed in the forming resin of the light guide. The light guide in which the light scattering particles are dispersed and mixed scatters emission light H emitted from the front end of the optical fiber 62 and thereby can output the scattered light to a broad area outside the light guide.

The light scattering particles function as an optical path changer that changes the direction of the emission light H emitted from the front end of the optical fiber 62.

Figure 6:
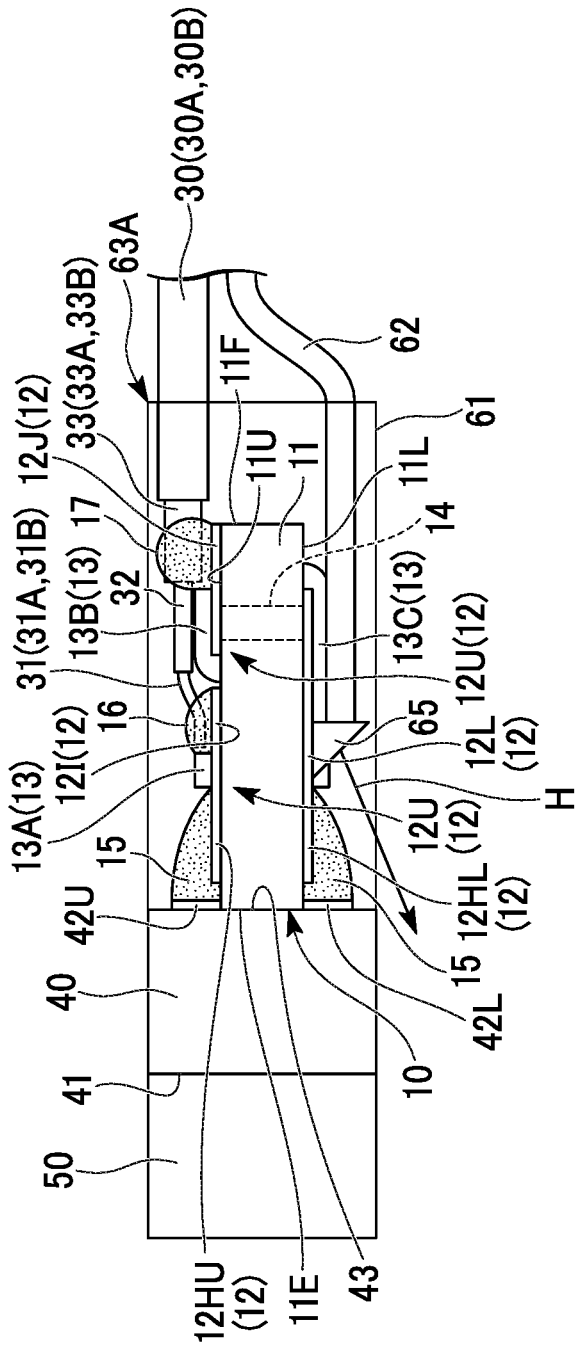
FIG. 6 is a view showing a modified example of a structure-front-end support of the imaging module shown in FIG. 1 and is a cross-sectional view showing a position close to the structure-front-end support having a prism (optical path changer) provided inside a light guide.

Moreover, as shown in FIG. 6, as the configuration of the structure-front-end support, a configuration may be adopted in which a prism 65 (optical path changer) that refracts the emission light H emitted from the front end of the optical fiber 62 and thereby emits the light from the light guide 61 to the outside is provided in the light guide 61.

The structure-front-end support 63A shown in FIG. 6, the front-end portion of the optical fiber 62 and the prism 65 are provided at the portion opposite to the signal cable 30 via the first substrate 10 in a vertical direction of the structure-front-end support 63A that coincides with the thickness direction of the first substrate 10 (in the vertical direction in FIG. 6, the upper side in FIG. 6 is the upper side in the vertical direction, and the lower side in FIG. 6 is the lower side in the vertical direction), that is, at the lower side of the first substrate 10.

The prism 65 of the structure-front-end support 63A shown in FIG. 6 refracts the emission light H emitted from the front end of the optical fiber 62, changes the direction of the emission light H to be inclined with respect to the first substrate 10, guides the emission light forward from the light guide 61 so as to avoid the solid-state image sensing device 40, and emits the light.

Instead of the prism 65, as the configuration of the structure-front-end support, a configuration may be adopted in which a mirror (optical path changer) that reflects the emission light H emitted from the front end of the optical fiber 62, changes the direction of the emission light, and allows the emission light to be emitted from the light guide 61 is provided in the light guide 61.

Figure 7A:
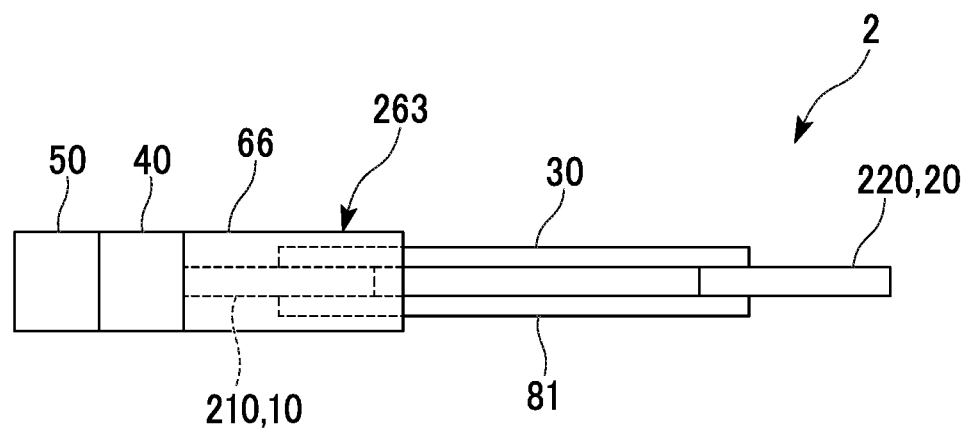
FIG. 7A is an explanatory diagram showing an imaging module according to one or more embodiments of the invention, showing a schematic configuration of the imaging module using a shape-memory wire as a linear structure, and showing a state where the shape-memory wire that is not subjected to current passage heating is extended straight together with the signal cable.
Figure 7B:
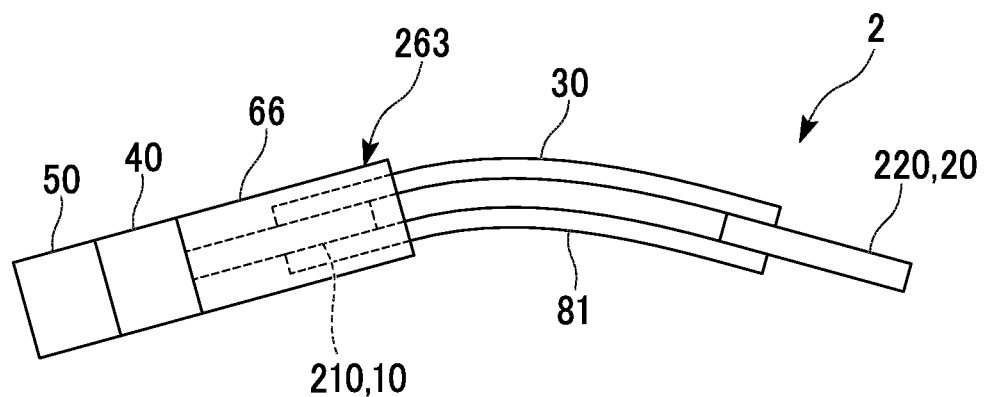
FIG. 7B is an explanatory diagram showing an imaging module according to one or more embodiments of the invention, showing a schematic configuration of the imaging module using a shape-memory wire as a linear structure, and showing a state where the shape-memory wire is returned (restored) to have the original form having a circular arc shape by current passage heating.

FIGS. 7A and 7B are views each showing a schematic configuration of an imaging module 2 according to one or more embodiments of the invention.

In FIGS. 7A and 7B, identical reference numerals are used for the elements which are identical to those of one or more embodiments described above, and the explanations thereof are omitted or simplified here.

Instead of the optical fiber 62 of the imaging module 1 shown in FIG. 1, the imaging module 2 shown in FIGS. 7A and 7B includes: a linear structure 81 (hereinbelow, also referred to as a shape-memory wire) formed of a current-passage-heating shape-memory alloy; and a grounding cable 82 (refer to FIG. 8) that is used to drive the shape-memory wire 81 by providing electric power (restoration of an original shape by current passage heating).

Here, the current-passage-heating shape-memory alloy means a shape-memory alloy which can be restored to an original shape by being electrically heated by using current passage heating.

As the current-passage-heating shape-memory alloy, a known material such as Ni—Ti alloy (nitinol) or Cu—Zn—Al alloy can be adopted, and particularly Ni—Ti alloy may be used therefor.

As shown in FIGS. 7A and 7B, the shape-memory wire 81 extends in a direction along the signal cable 30 and is disposed on the side of the signal cable 30 at which the first substrate 10 and the second substrate 20 are provided.

The front-end portion of the shape-memory wire 81 is disposed at the lower face 11L of the first substrate main body 11 and is fixed to the first substrate 10 (specifically, the first substrate main body 11) by a mold 66. The mold 66 is a resin or an adhesive (hardened material of the resin), and the front-end portion of the shape-memory wire 81 is implanted into the mold. The front-end portion of the shape-memory wire 81 shown in FIGS. 7A and 7B together with the first substrate 10 is implanted into the mold 66 and is fixed to the mold 66 and the first substrate 10 and is integrated into a body.

The mold 66 has a function as a support member (front-end support member for a linear structure) that fixes (supports) the front-end portion of the shape-memory wire 81 and is used to be attached to the first substrate 10.

Note that, it is only necessary that the mold 66 is configured to have a function as a support member (front-end support member for a linear structure) that fixes (supports) the front-end portion of the shape-memory wire 81 and is attached to the first substrate 10, it is not necessarily the configuration in which the first substrate 10 is implanted into the mold. For example, a configuration may be adopted in which the first substrate 10 is not implanted into the mold 66 made of the hardened material of the adhesive and the mold 66 is adhesively fixed to the lower face 11L of the first substrate main body 11.

The back-end portion of the shape-memory wire 81 is disposed on the lower face of the second substrate 20 and is fixed to the second substrate 20 (specifically, the second substrate main body 21).

As fixation of the back-end portion of the shape-memory wire 81 with respect to the second substrate 20, adhesive fixation using an adhesive, incorporation into one body using a resin mold, or the like can be adopted.

The shape-memory wire 81 has an original form which is curved and formed in a circular arc shape (bow shape) shown in FIG. 7B.

As shown in FIG. 7B, the shape-memory wire 81 becomes the original form by being heated and subjected to current passage heating. As a result, the signal cable 30 is also curved in a circular arc shape (bow shape) along the shape-memory wire 81.

On the second substrate 20 according to one or more embodiments of the invention, the imaging module 2 shown in FIGS. 7A and 7B includes a second substrate 220 having a configuration including: a power supply device connection terminal that is electrically connected to a power supply device that supplies electric power to the shape-memory wire 81 for current passage heating; and a driving power supply wiring that electrically connects the power supply device connection terminal and the back-end portion of the shape-memory wire 81.

A power supply device that is used for the current passage heating of the shape-memory wire 81 is electrically connected to the back-end portion of the shape-memory wire 81 via the second substrate 220.

Figure 8:
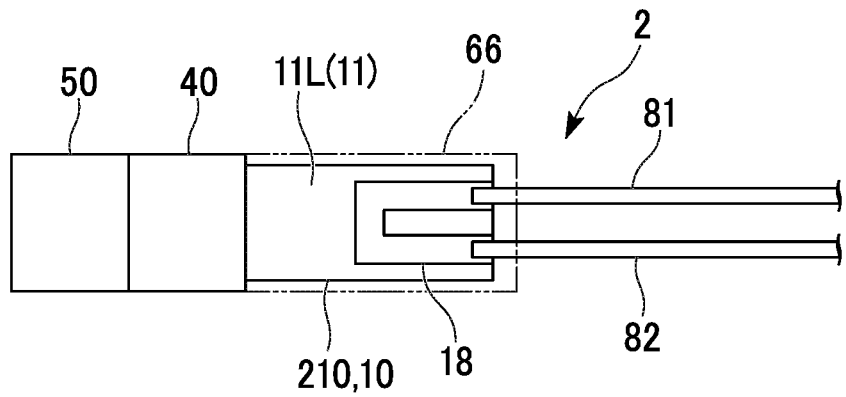
FIG. 8 is an explanatory diagram showing a relationship among the shape-memory wire, a grounding cable, and a grounding connection wiring of a lower surface side of the first substrate of the imaging module shown in FIGS. 7A and 7B, and is a view showing a region close to the structure-front-end support as seen from the lower surface side of a first substrate main body so as to see through a mold into which a front-end portion of the shape-memory wire and a front-end portion of the grounding cable are implanted and which fixes the front-end portion of the shape-memory wire and the front-end portion of the grounding cable to the first substrate.

As shown in FIG. 8, the grounding cable 82 is electrically connected to the front-end portion of the shape-memory wire 81 via a grounding connection wiring 18 formed on the lower face 11L of the first substrate main body 11.

The shape-memory wire 81 is subjected to current passage heating by power supply from the power supply device and thereby can be restored to the original shape.

In FIGS. 7A and 7B, the back-end portion of the shape-memory wire 81 is electrically connected to a power supply connection terminal formed on the lower face 21L of the second substrate main body 21. The second substrate 220 of the imaging module 2 shown in FIGS. 7A and 7B includes a second wiring having a structure in which the power supply connection terminal, the power supply device connection terminal, and the driving power supply wiring that electrically connects the power supply connection terminal and the power supply device connection terminal are added to the second wiring of the second substrate 20 according to one or more embodiments of the invention.

The back-end portion of the shape-memory wire 81 is electrically connected to the power supply device electrically connected to the power supply device connection terminal of the second substrate 220 via the driving power supply wiring.

The imaging module 2 according to one or more embodiments of the invention includes a first substrate 210 having a structure in which the grounding connection wiring 18 is added to the first substrate 10 according to one or more embodiments of the invention. The first substrate 210 of the imaging module 2 includes a first wiring having a structure in which the grounding connection wiring 18 is added to the first wiring 12 of the first substrate 10 according to one or more embodiments of the invention.

As shown in FIG. 8, the grounding cable 82 is provided along the shape-memory wire 81. The grounding cable 82 extends along the signal cable 30 together with the shape-memory wire 81 and is disposed on the signal cable 30 at which the first substrate 210 and the second substrate 220 are provided.

The front-end portion of the grounding cable 82 is attached to the grounding connection wiring 18 of the first substrate 210 by soldering or the like. Furthermore, the front-end portion of the grounding cable 82 is implanted into the forming resin of the mold 66, is fixed to the mold 66, the first substrate 210, and the front-end portion of the shape-memory wire 81, and is integrated into one body.

The imaging module 2 includes a structure-front-end support 263 having a configuration in which the front-end portion of the shape-memory wire 81 and the front-end portion of the grounding cable 82 are integrated by the forming resin of the mold 66 on the first substrate 210.

The imaging module 2 is used in a state where the back-end portion of the grounding cable 82 is electrically connected to a grounding device.

Note that, the grounding cable 82 has flexibility and can be curved together with the signal cable 30 with a user's finger.

When electric power is not provided to the shape-memory wire 81, since the shape-memory wire has flexibility, it is possible to bend the wire with a user's finger. For example, as shown in FIG. 7A, the shape-memory wire 81 to which electric power is not provided can be in a state of being extended straight together with the signal cable 30, or can be in a state of being curved or bent together with the signal cable 30.

As shown in FIG. 7B, the shape-memory wire 81 becomes the original form by being heated and subjected to current passage heating. Consequently, the signal cable 30 and the grounding cable 82 (not shown in FIGS. 7A and 7B) are also curved in a circular arc shape (bow shape) along the shape-memory wire 81.

Note that, the power supply device can switch between power supply to the shape-memory wire 81 (provision of electric power) and release of the power supply (release of provision of electric power) in accordance with a user's operation.

By inserting the imaging module 2 into, for example, one lumen of a catheter that includes a plurality of lumens in advance, it is possible to easily introduce the catheter into vitals having branch such as a blood vessel or a bronchus.

Figure 9A:
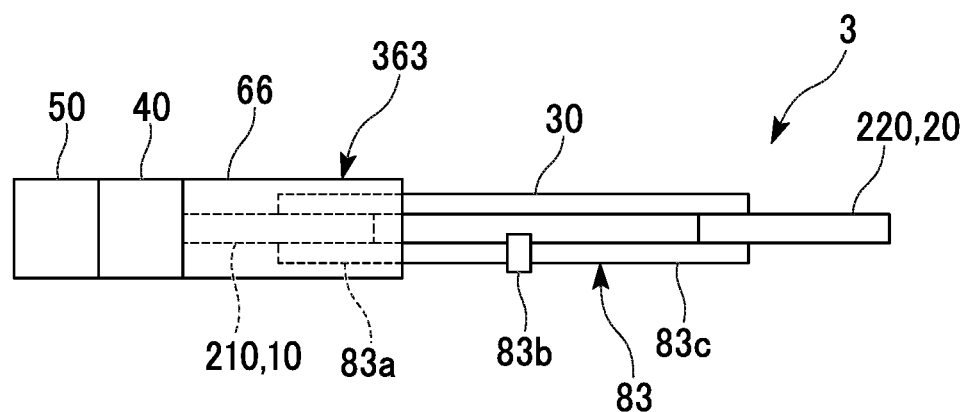
FIG. 9A is a view showing a configuration (modified example) in which the shape-memory wire of the imaging module shown in FIGS. 7A and 7B is replaced with a shape-memory unit-incorporated structure having a configuration in which the shape-memory wire is electrically connected to a front side of a power supply cable, and showing a state where the shape-memory wire that is not subjected to current passage heating is extended straight together with the signal cable.
Figure 9B:
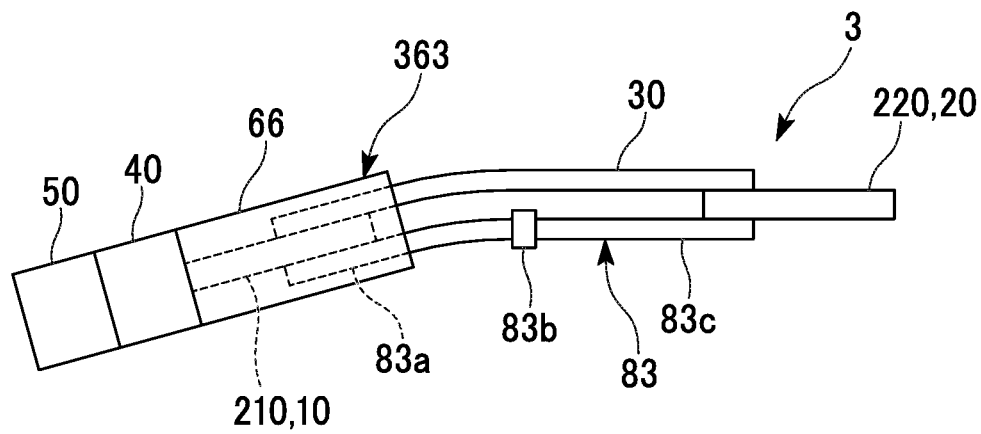
FIG. 9B is a view showing a configuration (modified example) in which the shape-memory wire of the imaging module shown in FIGS. 7A and 7B is replaced with a shape-memory unit-incorporated structure having a configuration in which the shape-memory wire is electrically connected to a front side of a power supply cable, and showing a state where the shape-memory wire is returned (restored) to have the original form having a circular arc shape by current passage heating.

As shown in FIGS. 9A and 9B, instead of the shape-memory wire 81, as the configuration of the imaging module, a configuration may be adopted which uses a linear structure 83 (hereinbelow, also referred to as a shape-memory unit-incorporated structure) in which a power supply cable 83c is electrically connected to shape-memory wire 83a via a relay substrate 83b.

An imaging module 3 shown in FIGS. 9A and 9B is configured to use a shape-memory unit-incorporated structure 83 instead of the shape-memory wire 81 of the imaging module 2 shown in FIGS. 7A, 7B, and 8.

As shown in FIGS. 9A and 9B, the shape-memory unit-incorporated structure 83 is provided along the signal cable 30 so that the front-end portion of the shape-memory wire 83a which is opposite to the relay substrate 83b is fixed to the first substrate 210 (the first substrate main body 11) and the back-end portion of the power supply cable 83c which is opposite to the relay substrate 83b is electrically connected to a power supply connection terminal of the second substrate 220.

The shape-memory unit-incorporated structure 83 is disposed on the side of the signal cable 30 at which the first substrate 210 and the second substrate 220 are provided.

As a fixation structure in which the front-end portion of the shape-memory wire 83a is fixed to the first substrate 210 (the first substrate main body 11), a structure can be adopted which is the same as the fixation structure in which the shape-memory wire 81 of the imaging module 2 shown in FIGS. 7A, 7B, and 8 is fixed to the first substrate 210 (the first substrate main body 11). In FIGS. 9A and 9B, the front-end portion of the shape-memory wire 83a is implanted into the formation material of the mold 66, is fixed to the mold 66, the first substrate 210, and the front-end portion of the shape-memory wire 81, and is incorporated into a body. The mold 66 functions as a support member (front-end support member for a linear structure body) that fixes (supports) the front-end portion of the shape-memory wire 83a and is attached to the first substrate 210 (the first substrate main body 11).

The imaging module 3 includes a structure-front-end support 363 having a configuration in which the front-end portion of the shape-memory wire 83a and the front-end portion of the grounding cable 82 are integrated by the formation material of the mold 66 on the first substrate 210.

The length of the shape-memory wire 83a is less than or equal to half of the overall length of the shape-memory unit-incorporated structure 83.

However, the shape-memory wire 83a ensures a length such that the shape-memory wire has the portion extending from the mold 66 toward the back side and is located between the mold 66 and the relay substrate 83b.

The shape-memory wire 83a has an original form which is curved and formed in a circular arc shape (bow shape) shown in FIG. 9B. As shown in FIG. 9B, the shape-memory wire 83a becomes the original form by being heated and subjected to current passage heating.

When electric power is not provided to the shape-memory wire 83a, since the shape-memory wire has flexibility, it is possible to bend the wire with a user's finger.

The imaging module 3 shown in FIGS. 9A and 9B is configured so that, by driving the shape-memory wire 83a by providing electric power thereto (restoration of an original shape by current passage heating), it is possible to bend only the region that is along the shape-memory wire 83a and is from the center to the portion at the front-end side in the longitudinal direction of the signal cable 30.

Figure 10A:
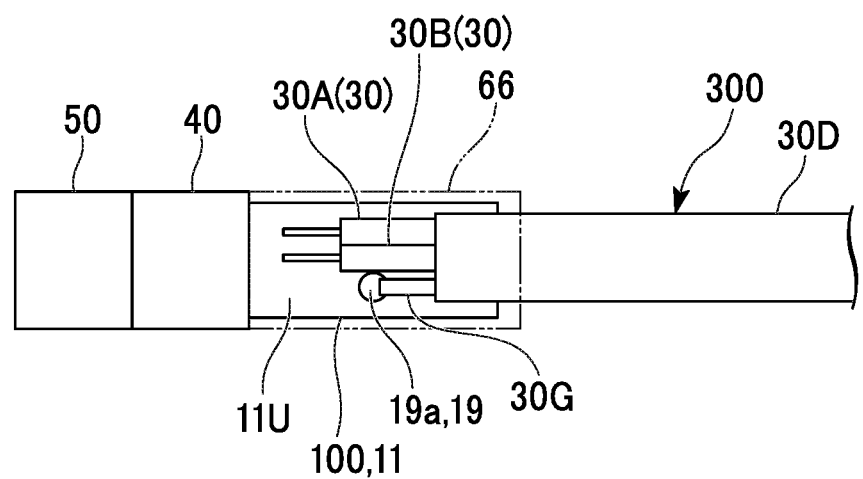
FIG. 10A is an explanatory diagram showing a ground-securement structure according to one or more embodiments of the invention in which the grounding cable provided to the signal cable is electrically connected to the shape-memory wire via the grounding connection wiring of the first substrate, and showing a region close to the structure-front-end support as seen from the upper surface side of the first substrate main body so as to see through the mold.
Figure 10B:
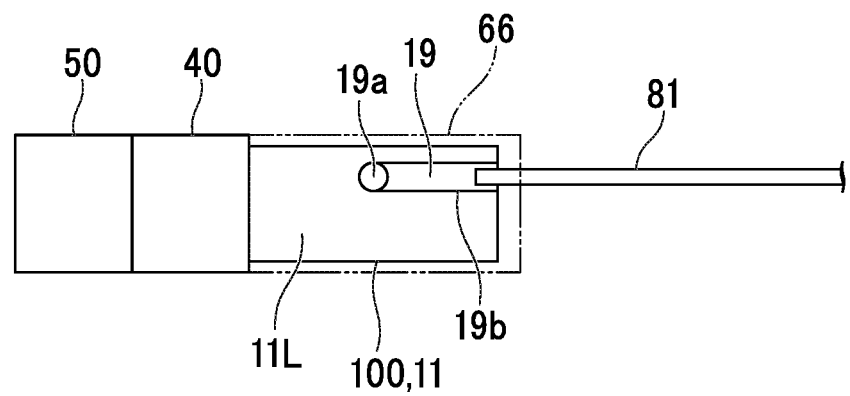
FIG. 10B is an explanatory diagram according to one or more embodiments of the invention showing a ground-securement structure in which the grounding cable provided to the signal cable is electrically connected to the shape-memory wire via the grounding connection wiring of the first substrate, and showing a region close to the structure-front-end support as seen from the lower surface side of the first substrate main body so as to see through the mold.

As shown in FIGS. 10A and 10B, instead of the grounding cable 82, a signal cable 300 having a configuration in which a grounding cable 30G in addition to the first coaxial cable 30A and the second coaxial cable 30B are provided inside the outer coating 30D may also be adopted in the imaging modules 2 and 3.

FIGS. 10A and 10B are explanatory diagrams showing a relationship of electrical connection between the grounding cable 30G of the signal cable 300 which is adopted instead of the grounding cable 82 of the imaging module 2 and the shape-memory wire 81.

Note that, in FIGS. 10A and 10B, wirings other than the grounding connection wiring 19 formed on the upper face 11U and the lower face 11L of the first substrate main body 11 are not shown in the figure for easily understanding a relation of connection among the grounding cable 30G, the shape-memory wire 81, and a grounding connection wiring 19 formed on the first substrate 10.

As shown in FIGS. 10A and 10B, in the case where the signal cable 300 including the grounding cable 30G is adopted, a first substrate 100 on which the grounding connection wiring 19 including a through-hole interconnection 19a penetrating through the first substrate 10 in a thickness direction of the first substrate main body 11 is formed is adopted in the imaging module. The grounding connection wiring 19 shown in FIGS. 10A and 10B includes the through-hole interconnection 19a and a wiring pattern 19b formed on the lower face 11L of the first substrate main body 11.

The grounding connection wiring 19 shown in FIGS. 10A and 10B does not have a wiring pattern on the upper face 11U of the first substrate main body 11. However, as the grounding connection wiring 19, a configuration may also be adopted which includes: a wiring pattern formed on each of the upper face 11U and the lower face 11L of the first substrate main body 11; and a through-hole interconnection that electrically connects wiring patterns on the upper face 11U and the lower face 11L of the first substrate main body 11 to each other.

In FIGS. 10A and 10B, the front-end portion of the part of the grounding cable 30G of the signal cable 300 which extends from the outer coating 30D of the signal cable 300 is electrically connected to the grounding connection wiring 19 on the upper surface side of the first substrate 100 by soldering or the like. The shape-memory wire 81 is electrically connected to the grounding connection wiring 19 on the lower surface side of the first substrate 100 by soldering or the like.

Accordingly, the shape-memory wire 81 is electrically connected to the grounding cable 30G of the signal cable 300 via the grounding connection wiring 19.

The electrical connection structure in which the first substrate 100 having the grounding connection wiring 19 formed thereon is adopted and the shape-memory wire 81 is electrically connected to the grounding cable 30G of the signal cable 300 via the grounding connection wiring 19 is applicable to the electrical connection structure in which the grounding cable 30G of the signal cable 300 which is adopted instead of the grounding cable 82 of the imaging module 3 shown in FIGS. 9A and 9B is electrically connected to the shape-memory unit-incorporated structure 83.

In the imaging modules 2 and 3 shown in FIGS. 7A, 8, 9A, and 9B as an example, the shape-memory wires 81 and 83a function as an actuator that bends a signal cable.

In the case where using the imaging modules 2 and 3 shown in FIGS. 7A, 8, 9A, and 9B as an example so as to be accommodated in a tube such as a catheter, it is only necessary to use a tube in which a cross sectional size required for accommodating the solid-state image sensing device 40 is ensured, and an increase in a diameter of a tube for accommodating a linear structure (the shape-memory wire 81 and the shape-memory unit-incorporated structure 83) can be avoided. As a result, a shape-memory wire that functions as an actuator bending a signal cable can be provided in an imaging module without an increase in a diameter of the tube.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

As the imaging module, a configuration which does not include a lens housing that accommodates a lens unit therein may be adopted.

As the structure-front-end support of the imaging module, various configurations which can fix the front-end portion of the linear structure to the first substrate may be adopted. However, the structure-front-end support is configured such that, the front-end portion of a signal cable which is close to the first substrate, the front-end portion of the linear structure, and the structure-front-end support are located within a projected area of the image-sensing device which is projected toward the back surface side.

What is claimed is:
1. An imaging module comprising:
an image-sensing device;
a first substrate comprising a wiring and is disposed on a back surface side of the image-sensing device that is opposite an imaging surface of the image-sensing device and extends from the image-sensing device to the opposite side of the imaging surface;
a signal cable comprising:
a signal line electrically connected to the image-sensing device via the wiring of the first substrate; and
an outer coating accommodating the signal line;
a second substrate comprising a wiring electrically connected to a rear end of the signal line opposite a front end of the signal line connected to the wiring of the first substrate; and
a flexible linear structure disposed along the signal cable, wherein
each of the first substrate and the second substrate comprises a cable terminal electrically connected to the signal line on only one surface of the first substrate and on only one surface of the second substrate,
each of the wiring of the first substrate and the wiring of the second substrate is electrically connected to the signal line via the cable terminal,
if the signal cable extends straight without torsional deformation, where the one surface of the first substrate is an upper surface and a surface of the first substrate opposite the upper surface is a lower surface, then:
the one surface of the second substrate is an upper surface, and
a surface of the second substrate opposite the upper surface of the second substrate is a lower surface, and
the flexible linear structure extends in a direction along the signal cable from a front-end portion of the flexible linear structure, wherein
the front-end portion of the flexible linear structure is supported by a structure-front-end support and the first substrate, and
the flexible linear structure is disposed on a side of the signal cable where the first substrate and the second substrate are disposed,
an entirety of the first substrate, the front-end portion of the flexible linear structure, and the structure-front-end support are disposed within an outline of the back surface side of the image-sensing device when viewed from the back surface side, the structure-front-end support comprises a light guide, and the flexible linear structure comprises an optical fiber.

2. The imaging module according to claim 1, wherein the light guide is made of transparent resin, the first substrate is implanted in the light guide, and the front-end portion of the optical fiber is fixed and inserted into the light guide.

3. The imaging module according to claim 2, wherein the light guide comprises an optical path changer that reflects, refracts, or scatters light emitted from a front end of the optical fiber, and using the optical path changer, the light guide outputs the light from the light guide to the outside of the light guide.

4. The imaging module according to claim 1, wherein the flexible linear structure comprises a current-passage-heating shape-memory alloy.

5. The imaging module according to claim 1, wherein a portion or an entirety of the flexible linear structure is a current-passage-heating shape-memory alloy, and a back-end portion of the flexible linear structure is attached to the second substrate.

6. The imaging module according to claim 1, wherein the front-end portion of the flexible linear structure is disposed on a second surface side of a first substrate main body opposite a first surface side of the first substrate main body where the cable terminal of the first substrate is disposed.

7. The imaging module according to claim 1, wherein the wiring of the first substrate comprises:

a first substrate upper face wiring disposed on a first surface of a first substrate main body where the cable terminal of the first substrate is disposed;

a first substrate lower face wiring disposed on a second surface of the first substrate main body opposite the first surface of the first substrate main body; and a through-hole interconnection that penetrates through the first surface and the second surface of the first substrate main body and electrically connects the first substrate upper face wiring to the first substrate lower face wiring, wherein the image-sensing device comprises a plurality of image-sensing device electrodes disposed on the back surface of the image-sensing device, each of the plurality of image-sensing device electrodes is arranged on both sides of the first substrate in a thickness direction, and each of the first substrate upper face wiring and the first substrate lower face wiring is electrically connected to an image-sensing device electrode among the plurality of image-sensing device electrodes.

8. The imaging module according to claim 1, wherein the signal cable comprises a plurality of the signal line that are laterally disposed inside the outer coating, and the first substrate and the second substrate are attached to the signal cable on a same side of an array plane of the plurality of the signal lines and are directed along the array plane.

\* \* \* \* \*